(12) United States Patent
Lichtblau

(10) Patent No.: US 8,791,441 B1
(45) Date of Patent: Jul. 29, 2014

(54) ULTRAVIOLET RADIATION SYSTEM

(71) Applicant: George Jay Lichtblau, New Canaan, CT (US)

(72) Inventor: George Jay Lichtblau, New Canaan, CT (US)

( * ) Notice: Subject to any disclaimer, the term of this patent is extended or adjusted under 35 U.S.C. 154(b) by 0 days.

(21) Appl. No.: 14/048,418

(22) Filed: Oct. 8, 2013

Related U.S. Application Data

(60) Provisional application No. 61/870,410, filed on Aug. 27, 2013.

(51) Int. Cl.
- *A61L 2/10* (2006.01)
- *A61L 2/24* (2006.01)
- *A61L 9/20* (2006.01)

(52) U.S. Cl.
CPC ............. *A61L 2/10* (2013.01); *A61L 2202/25* (2013.01); *A61L 9/20* (2013.01); *A61L 2/24* (2013.01)
USPC ................................. 250/504 R; 250/455.11

(58) Field of Classification Search
CPC ........................................................ A61L 2/10
USPC .................................................... 250/455.11
See application file for complete search history.

(56) References Cited

U.S. PATENT DOCUMENTS

| | | | | |
|---|---|---|---|---|
| 5,326,542 | A * | 7/1994 | Sizer et al. | 422/291 |
| 5,780,860 | A | 7/1998 | Gadgil et al. | |
| 6,424,285 | B1 * | 7/2002 | Perdue et al. | 341/176 |
| 6,656,424 | B1 * | 12/2003 | Deal | 422/3 |
| 6,855,295 | B2 | 2/2005 | Kulp | |
| 6,911,177 | B2 * | 6/2005 | Deal | 422/24 |
| 7,687,997 | B2 | 3/2010 | Gaertner et al. | |
| 8,080,212 | B2 | 12/2011 | Speer et al. | |
| 8,167,542 | B1 * | 5/2012 | Owusu | 415/127 |
| 2003/0209420 | A1 * | 11/2003 | Taylor et al. | 204/164 |
| 2004/0200975 | A1 | 10/2004 | Brown et al. | |
| 2005/0211640 | A1 * | 9/2005 | Snowball | 210/748 |
| 2006/0145092 | A1 * | 7/2006 | Gunn et al. | 250/474.1 |
| 2006/0278075 | A1 * | 12/2006 | Blackner | 95/57 |
| 2008/0194009 | A1 * | 8/2008 | Marentis | 435/283.1 |
| 2010/0028134 | A1 * | 2/2010 | Slapak et al. | 415/119 |

(Continued)

FOREIGN PATENT DOCUMENTS

WO    WO 2013/116566    8/2013

OTHER PUBLICATIONS http://www.globalindustrial.com/c/janitorial-maintenance/parking-lot-Supplies/safety-bollards-guards, fetched from archive.org, Aug. 24, 2011.*

(Continued)

*Primary Examiner* — Jack Berman
*Assistant Examiner* — James Choi
(74) *Attorney, Agent, or Firm* — Preti Flaherty Beliveau & Pachios LLP

(57) ABSTRACT

The present invention provides an ultraviolet radiation system which generates UVC radiation with maximal radiation output and little or no degradation in radiation output during operation of the lamps. The system provides UVC radiation at a wavelength of 253.7 nm, which is effective to kill or deactivate pathogens on surfaces irradiated by the emitted UVC radiation and is simultaneously effective to decontaminate air which passes uniformly over the entire length of the UVC lamps. Uniformly flowing air cools the lamps to maximize the conversion efficiency of power input to the lamps to UVC radiation from the lamps, and at the same time decontaminates the flowing air such that air in the room is also decontaminated.

29 Claims, 4 Drawing Sheets

(56) References Cited

U.S. PATENT DOCUMENTS

| | | | |
|---|---|---|---|
| 2010/0032589 A1* | 2/2010 | Leben | 250/504 R |
| 2010/0202931 A1 | 8/2010 | Harris | |
| 2010/0266445 A1 | 10/2010 | Campagna | |
| 2012/0099249 A1* | 4/2012 | Duan et al. | 361/679.01 |
| 2012/0246863 A1* | 10/2012 | Douglas | 15/339 |
| 2012/0305787 A1 | 12/2012 | Henson | |
| 2013/0020942 A1* | 1/2013 | Voronov | 315/116 |
| 2013/0052882 A1* | 2/2013 | Brausen | 439/718 |
| 2013/0099249 A1* | 4/2013 | Forcier et al. | 257/76 |
| 2013/0256560 A1* | 10/2013 | Yerby | 250/455.11 |
| 2014/0044590 A1* | 2/2014 | Trapani | 422/3 |

OTHER PUBLICATIONS

Important Informations about UVC-Lamps, www.z-e-d.com, pp. L&S-A 1-L&S-A 3, Oct. 2011.

\* cited by examiner

ULTRAVIOLET RADIATION SYSTEM

CROSS REFERENCE TO RELATED APPLICATIONS

This application claims the benefit under 35 U.S.C. §119 (3) of U.S. Provisional Patent Application No. 61/870,410, entitled "Ultraviolet Radiation System" filed Aug. 27, 2013 which is herein incorporated by reference in its entirety for all purposes.

BACKGROUND OF THE INVENTION

It is known that UVC radiation is effective in killing or deactivating pathogens in air, water and on exposed surfaces. UVC radiation is ultraviolet radiation having wavelengths in the shortwave C band and radiation in that band having a wavelength of 253.7 nm is reorganized to provide effective germicidal action. UVC lamps have been developed and are available for such germicidal or decontamination purposes. In general these lamps are low pressure, high output mercury or amalgam lamps.

It is also known that the operating temperature of UVC lamps affects their radiation output and that the lamps should be preferably cooled to provide efficient output. The optimum lamp operating temperature for low pressure, high output mercury lamps is 107° F. and for low pressure, high output amalgam lamps is 180° F. Lamp efficiency is especially important since electrical power for a UVC system is in most instances, limited to that available from standard 15A, 120 VAC wall outlets. Available power drawn is therefore limited to 1800W. However, known systems presently on the market, such as those listed in Appendix A hereto, have made no attempt to control lamp temperature to maintain lamp efficiency. It has been found that known systems suffer decreases in lamp output of about 60% or more as the lamps heat up, which can occur in a very short time of about 3 minutes.

Published application 2012/0305787 shows a surface disinfection system having a UVC lamp mounted on a portable base unit and contained within a transparent sleeve. Air from a variable speed fan is blown through the sleeve and the temperature of the lamp is measured and used to control the fan speed to maintain the lamp at an optimum operating temperature.

Published application 2003/0052279 shows a UV irradiation apparatus for decontaminating the surface of an object such as a semiconductor wafer. An array of UV lamps are arranged adjacent to a mirrored surface. The mirrored surface has openings of varying size to provide air flow in amounts to provide uniform cooling of the lamps.

U.S. Pat. Nos. 6,656,424 and 6,911,177 show an ultraviolet area sterilizer which employs a circular array of ultraviolet lamps on a movable dolly. Reflected radiation is measured at various locations in a room being irradiated and the lamps are turned off when the reflected light exceeds a predetermined level.

Despite the stated desire to control the temperature of UVC lamps in conventional systems such as those described in the references noted above, known systems have not attempted to achieve this stated object.

It would be beneficial to provide an ultraviolet radiation system for germicidal and decontamination purposes in which the UVC output is maintained at or near its maximum level without significant degradation in radiation output caused by heating of the lamps during operation and the same ultraviolet radiation can kill pathogens in the air in the room and on surfaces directly and indirectly radiated.

BRIEF SUMMARY OF THE INVENTION

The present invention provides an ultraviolet radiation system which generates UVC radiation with maximal radiation output and little or no degradation in radiation output during operation of the lamps. The system provides UVC radiation at a wavelength of 253.7 nm, which is effective to kill or deactivate pathogens on surfaces irradiated by the emitted UVC radiation and is simultaneously effective to decontaminate air which passes uniformly over the entire length of the UVC lamps. Uniformly flowing air cools the lamps to maximize the conversion efficiency of power input to the lamps to UVC radiation from the lamps, and at the same time decontaminates the flowing air such that air in the room is also decontaminated.

The system in one embodiment comprises a housing having an air chamber with an open upper end and a closed lower end. A plurality of UVC lamps is disposed about the side walls of the housing and is mechanically and electrically connected to the housing by suitable connectors or fittings. The housing side walls have their outer surfaces oxidized or otherwise coated to maximize the reflectance of UVC radiation. A fan or blower is located at the top of the air chamber. Vent openings are provided through the side walls of the housing in positions to direct air from the fan onto the entire length of the lamps. One or more UVC sensors are provided to monitor the output of the lamps. In the event that one or more lamps are detected to be generating less than the designated UVC output, the system may be turned off and/or an indicator may be activated to denote improper or failed lamp operation. A UVC sensor can be provided for each lamp to provide an indication of that lamp failure. Alternatively a sensor can be provided for a group of lamps to provide an indication of a failure in any one or more lamps of the group. One or more passive infrared sensors or other motion detectors can be provided to detect the presence of a person in the room or area where the system is operating. If a person is detected, the system can be turned off and an indicator activated to denote that system operation was interrupted by reason of intrusion in the room being irradiated.

The system is typically mounted on a dolly or other rolling base to provide for ready transport into and out of areas to be decontaminated. Preferably the system is controlled via a remote control device which communicates with the system by infrared or by radio frequency signals. Controls can also be provided on the system itself for direct control of the system. AC electricity for powering the system is monitored for a possible ground fault condition by a ground fault interrupter (GFI) built into or coupled to the power supply of the system. Electronic ballasts for the lamps are mounted inside the air chamber, and air flow in the chamber assists in cooling the ballasts during operation. Protective guard elements can be provided around the perimeter of the system to prevent the lamps from being struck inadvertently by contact with tables, beds or other furniture or obstructions in the room or area in which the system is placed for use.

The UVC system in accordance with the invention produces a UVC radiation output which is two times or more greater than the output produced by uncooled lamps and typically about 60% higher than achieved by conventional UVC radiation systems.

BRIEF DESCRIPTION OF THE SEVERAL VIEWS OF THE DRAWINGS

The invention will be more fully described in the following detailed description in conjunction with the drawings, in which.

DETAILED DESCRIPTION OF THE INVENTION

Cross Reference to Related Applications

This application claims the benefit under 35 U.S.C. §119 (3) of U.S. Provisional Patent Application No. 61/870,410, entitled "Ultraviolet Radiation System" filed Aug. 27, 2013 which is herein incorporated by reference in its entirety for all purposes.

Figure 1:
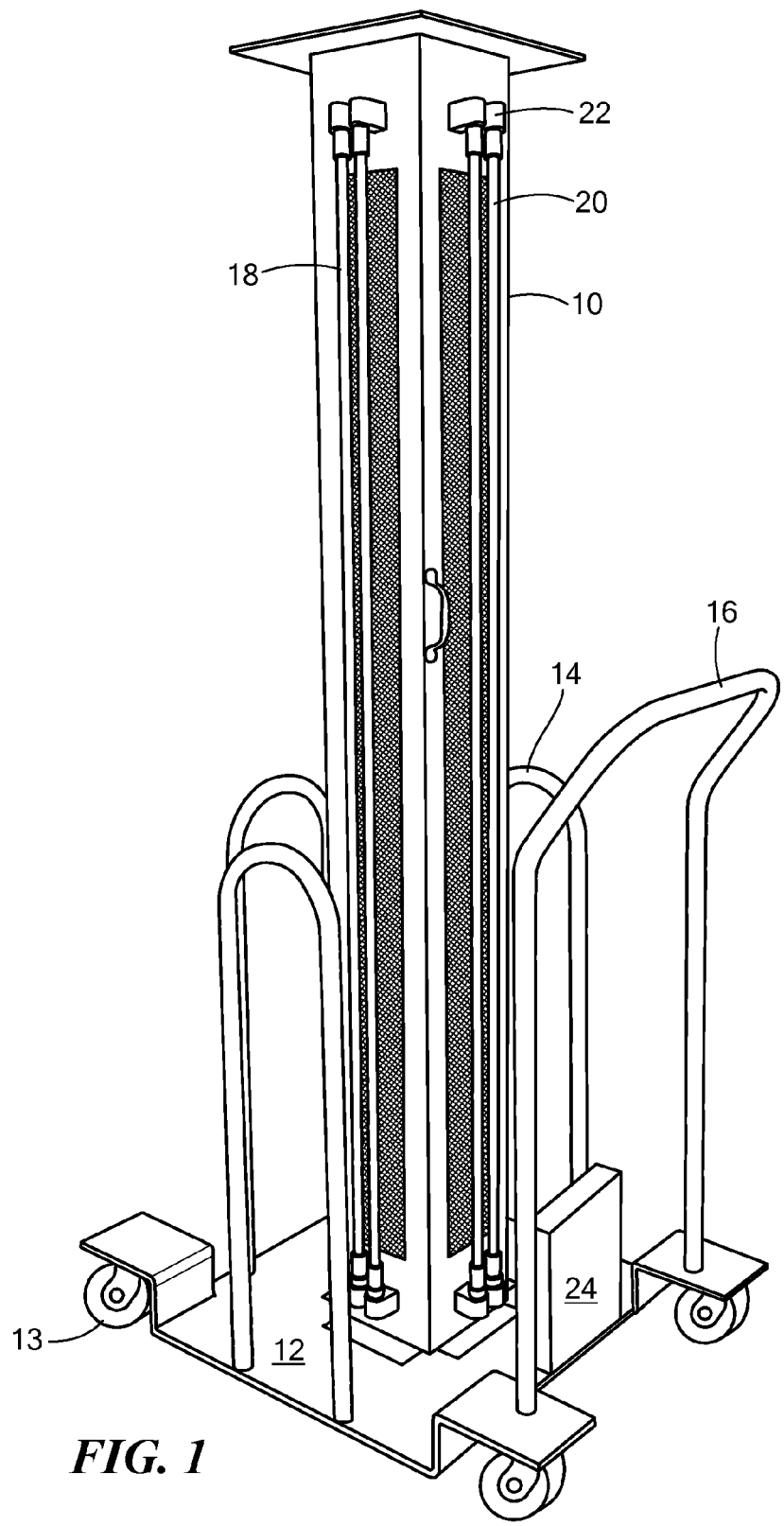
FIG. 1 is a pictorial view of one embodiment of the UVC radiation system in accordance with the invention.
Figure 2:
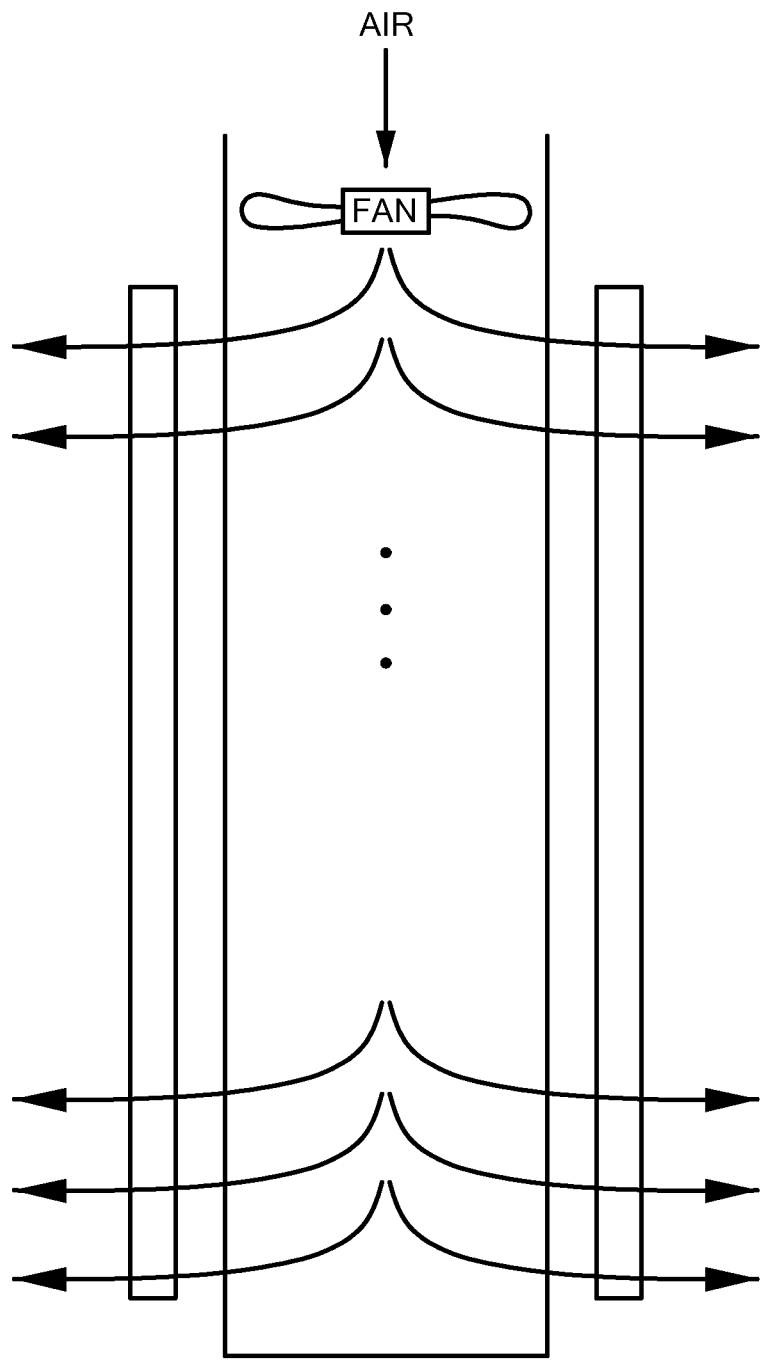
FIG. 2 is a diagrammatic elevation view of the embodiment of FIG. 1 illustrating the air flow.

One embodiment of an ultraviolet radiation system in accordance with the invention is illustrated in FIG. 1. A square enclosure or housing 10 is supported on a wheeled base or dolly 12 having four wheels or casters 13 positioned at corners of the base as shown. The enclosure 10 has air vent openings 18 through each side wall of the enclosure as described below. A pair of UVC lamps 20 are disposed at each side wall of the enclosure 10 and are electrically and mechanically mounted to the enclosure by connectors 22. The lamps are typically low pressure, high power mercury or amalgam vapor lamps which radiate UVC radiation. The pair of lamps at each side wall of the enclosure confront the vent openings in the respective side walls of the enclosure which pattern of openings are substantially coextensive with the length of the lamps. A fan or blower, not visible in FIG. 1, is mounted at the upper end of the enclosure 10 and is operative to direct an air stream downward through the enclosure. The air stream is vented through the openings 18 and thence across the lamps 20 to provide cooling of the lamps substantially along their entire length, as illustrated schematically in FIG. 2. The air flow is sufficient to maintain the operating temperature of the lamps at a level to achieve UVC radiation from the lamps at their maximum rated capacity. The eight lamps arranged in pairs around the housing provide 360° radiation coverage of the room in which the system is operating. Electronic ballasts for the UVC lamps are located inside the enclosure 10. The electronic controls and sensors are mounted in a housing 24 or control panel which can be mounted on the base 12 or on handle 16 or other convenient location. The controls may include a timer which is adjustable to determine the operating time for the system to govern the amount of radiation provided in the area for decontamination.

Figure 4:
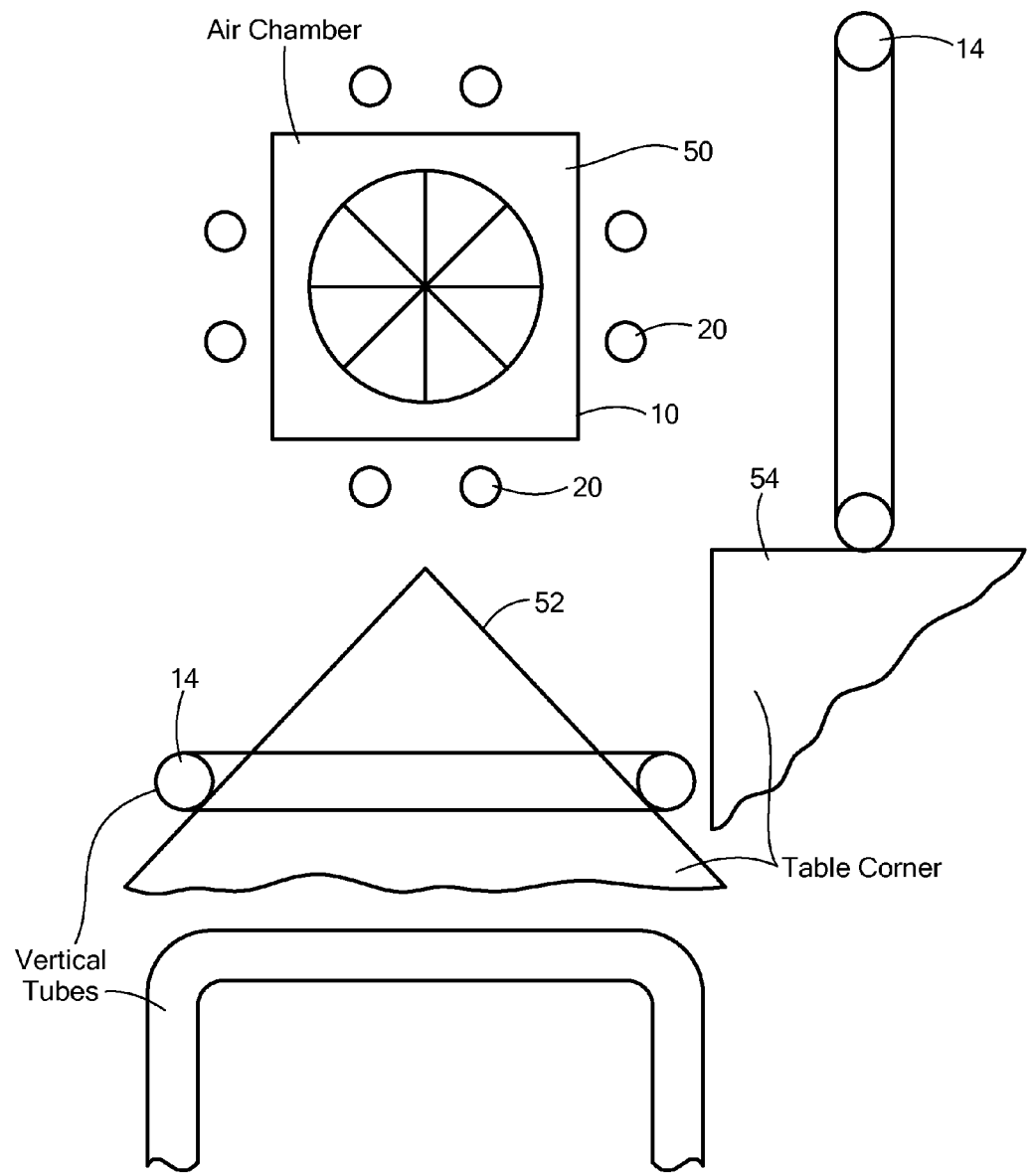
FIG. 4 is a diagrammatic top view of an embodiment of the invention illustrating the protective guard elements.

U shaped tubes 14 are positioned on three or four sides of the base as illustrated, and a generally U shaped handle 16 may be positioned on one side of the base as shown. The spacing of the legs of each U shaped tube 14 and the spacing between adjacent legs of adjacent tubes 14 are determined to protect the lamps from being broken or struck if the system is unintentionally pushed into a corner of a table, bed or other furniture item. A diagrammatic top view of an embodiment of the system is shown in FIG. 4. A square enclosure or housing 10 has a fan 50 at the top thereof, and two elongated UVC lamps 20 confronting each side of the housing 10. The spacing of the legs of each U shaped tube 14 are such that a corner 52 of a table or other object cannot intrude through the legs by an amount sufficient to contact the lamps 20. In addition the spacing between adjacent U shaped tubes is such to prevent intrusion of a table corner 54 or other object into contact with the lamps 20.

One or more of the sides of the enclosure 10 can be hinged or otherwise openable for access to the interior such as for maintenance and repair of components located within the enclosure.

The lamps are typically enclosed within a sleeve of protective material, which is UVC transmissive, such as Teflon, to avoid shattering of the lamp envelope if the lamp is struck by an object or mishandled.

In one implementation, the housing 10 is 66 inches in height and 7 inches square. The lamps are for example model GML-015 or similar mercury vapor lamps having a height of 60.5 inches. Such lamps are manufactured by American Ultraviolet, and Light-Sources, Inc. among others. The fan is a six inch muffin fan having an air flow capacity of 200 $ft^3$/min, and can be, for example, a model A1606V1H made by Sofasco International, Sunon Inc. and Nichibo Motor. The lamp temperature is maintained substantially at its optimum operating temperature to maximize the radiation output. The output efficiency is typically about 60% higher than that achieved by conventional UVC radiation systems.

Figure 3:
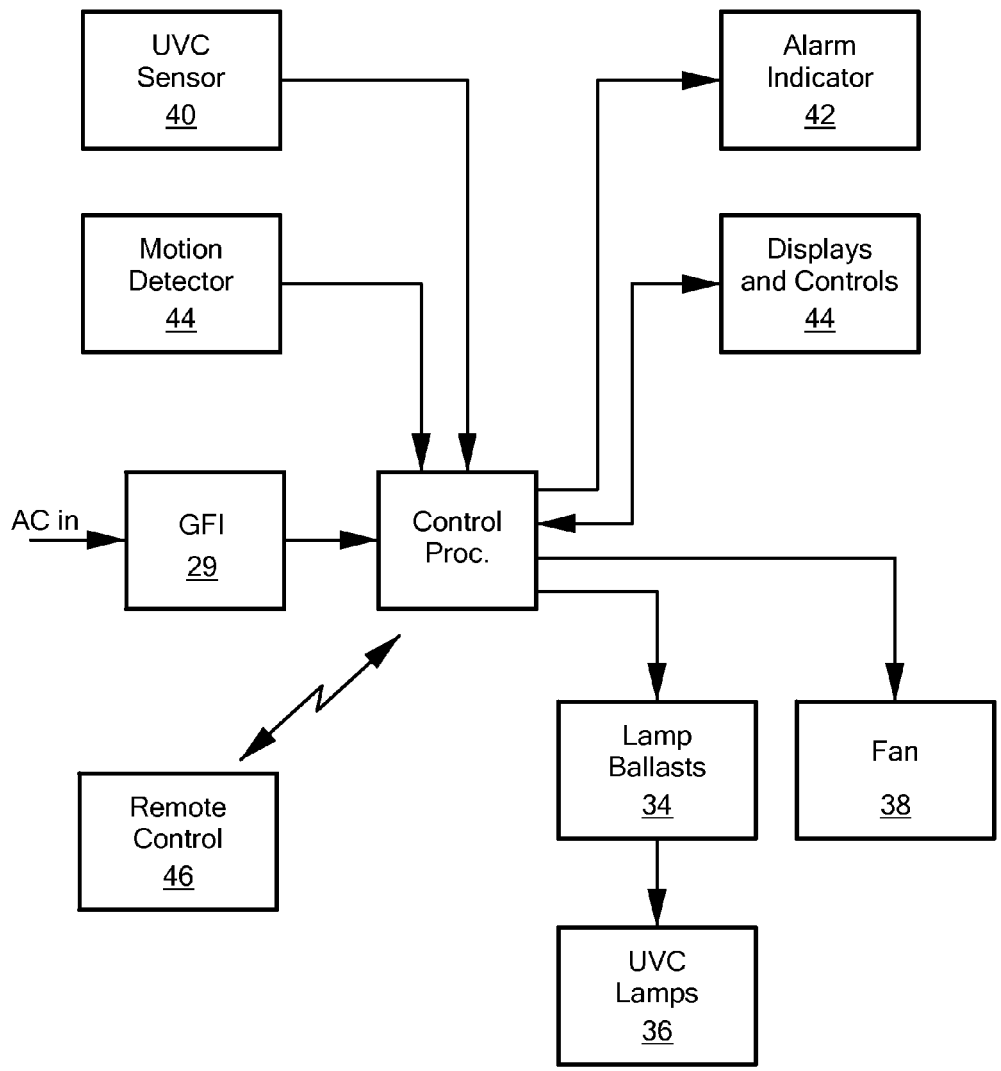
FIG. 3 is a block diagram of the system.

The system 13 illustrated in block diagram form in FIG. 3. AC input power is applied via a ground fault interrupter (GFI) 29 to a control processor 30. The input power is typically from a standard 120 or $2^{20}/_{240}$ volt outlet. The processor 30 is coupled to displays and controls 32 which include indicators or displays of system conditions and controls for system operation. The processor drives the lamp ballasts 34 which in turn drive the UVC lamps 36. The ballasts are preferably electronic ballasts. The processor also controls a fan 38 for lamp cooling. One or more UVC sensors 40 are provided to sense UVC radiation from the lamps 36 and to provide a signal to the processor 30 in the event that the sensed UVC radiation falls below a predetermined threshold level. This could occur for example in the event of a lamp failure. As an example, one UVC sensor can be disposed at each side of the enclosure (FIG. 1) to sense radiation from the pair of lamps on the respective sides. Upon the failure of any one or both of the lamps on a side, the applicable sensor will sense that failure by absence or decrease in the amount of sensed radiation, and provide a signal indication thereof to the power control processor. The power control processor in response to such signal from the sensor provides a signal to an alarm indicator 42 which can provide a visual, audible or other indicator of a fault condition. The alarm indicator may be included in the displays/controls unit 32. The control processor can also be operative in response to a signal from the sensor 40 to shut down the system. The shutdown may also be signified by a suitable alarm indication which may be a visual or audible alarm or an error message appearing on a system display. It will be appreciated that the degree of UVC monitoring can vary to suit particular system implementations. In one embodiment a single UVC sensor can be provided and positioned to sense loss or degradation of UVC radiation and to signal such condition to the power control processor 30. In another embodiment a UVC sensor can be provided to sense radiation from each individual lamp of an array of UVC lamps. In a further embodiment a UV sensor can be provided to sense radiation from two or more lamps of a larger group of lamps, as in the embodiment described above.

A motion sensor 44 is in communication with the control processor 30 and is operative to sense the motion of an intruder in the system site and to provide an output signal of such motion detection to the control processor 30. In response to such motion detection signal, the control processor can provide an alarm indication thereof such as via alarm indicator 42 and/or shut down the system.

A remote control 46 is in wireless communication with the processor 30 for remote operation of the system. The remote control typically employs an RF or infrared link and has operating controls and indicators for operating the system inside or outside of the site being irradiated.

It will be appreciated that the invention is not to be limited by the particular embodiments shown and that modifications and alternative implementations are contemplated and within the intended scope of the invention. For example, the fan or blower can be disposed at the bottom of the air chamber or other position therein to accomplish intended air flow. The number and type of UVC lamps can vary to suit intended radiation output and coverage. The physical configuration of the system may also be of many different forms. Accordingly, the invention is not to be limited by what has been particularly shown and described except as defined by the appended claims.

The invention claimed is:

1. An ultraviolet radiation system comprising;
   a plurality of UVC lamps providing UVC radiation;
   a housing having multiple side walls, each side wall being adjacent to at least one of the plurality of lamps, the housing having an air chamber therein and each side wall having air vent openings in a pattern which confront substantially the entire length of the at least one adjacent lamps;
   the plurality of UVC lamps and the air chamber arranged in a vertical orientation;
   the at least one lamp adjacent each of the side walls being positioned adjacent the pattern of air vent openings in that side wall;
   a fan in fluid coupling relationship with the housing to cause air to flow from the surrounding atmosphere into the housing and out through the pattern of vent openings in each side wall and across substantially the entire length of the at least one of the plurality of lamps adjacent each side wall into the surrounding atmosphere outside of the housing;
   the UVC radiation being effective to simultaneously kill pathogens in the air of the surrounding atmosphere outside of the housing and on radiated surfaces in the surrounding atmosphere outside of the housing directly and by reflected radiation;
   the flowing air being effective to cool the plurality of lamps to an optimum operating temperature to maximize the UVC radiation output from the plurality of lamps; and
   a power source for energizing the one or more lamps and fan.

2. The system of claim 1 wherein the fan is located at the top of the air chamber.

3. The system of claim 1 wherein the fan is located at the bottom of the air chamber.

4. The system of claim 1 wherein the fan is a muffin fan.

5. The system of claim 1 wherein the housing has side walls which are reflective to UVC radiation.

6. The system of claim 5 wherein the housing is aluminum.

7. The system of claim 6 wherein the side walls are oxidized to be reflective to UVC radiation.

8. The system of claim 1 including:
   a UVC radiation sensor to monitor UVC radiation from the one or more lamps and to provide a signal indicative thereof.

9. The system of claim 8 wherein the radiation sensor is made of an Indium Gallium Nitride based material.

10. The system of claim 1 wherein the one or more lamps are low pressure, high output mercury lamps.

11. The system of claim 1 wherein the one or more lamps are low pressure, high output amalgam lamps.

12. The system of claim 1 wherein the housing has four side walls and two lamps are disposed at each side wall.

13. The system of claim 1 wherein the housing has four side walls and one lamp is disposed at each side wall.

14. The system of claim 1 wherein the power source includes one or more electronic ballast to drive the one or more lamps.

15. The system of claim 14 wherein the at least one ballast is located in the air chamber.

16. The system of claim 1 wherein the housing is supported on a moveable dolly.

17. The system of claim 1 wherein the air flowing across the one or more lamps increases the UVC lamp output at least about two times the output of uncooled one or more lamps.

18. The system of claim 1 including a timer coupled to the power source and adjustable to set an operating time for the system.

19. The system of claim 1 wherein each one or more lamp is enclosed in a protective sleeve of UVC transmissive material.

20. The system of claim 19 wherein the protective sleeve is Teflon.

21. The system of claim 1 including a remote control in wireless communication with the system for control of the system.

22. The system of claim 1 including a control panel in the system for control thereof.

23. The system of claim 21 wherein the wireless communication is by light signals.

24. The system of claim 21 wherein the wireless communication is by RF signals.

25. The system of claim 1 including vertical guard elements outward of the one or more lamps and with spacing between the vertical guard elements to prevent a right angle corner of an object from reaching the UVC tubes to prevent the one or more lamps from being struck by objects in the area in which the system is installed.

26. The system of claim 25 wherein the guard elements include U shaped tubes disposed about the housing and spaced to prevent objects coming into contact with the one or more lamps.

27. The system of claim 1 wherein the power source includes a ground fault interrupter.

28. The system of claim 1 including a motion detector coupled to the system and operative to indicate the presence of a person in the area in which the system is operating.

29. An ultraviolet radiation system comprising:
   an elongated housing having a plurality of side walls, an upper portion open to the surrounding atmosphere, and a lower portion closed to the surrounding atmosphere;
   at least one tubular UVC lamp for providing UVC radiation, mounted adjacent to each respective side wall and having an electrical terminal at one or both ends;
   an upper and a lower connector associated with each side wall of the housing for mechanically and electrically connecting the respective electrical terminals of the at least one UVC lamp mounted adjacent the respective side walls of the housing;
   each side wall having an array of vent openings therethrough in a pattern substantially coextensive with the full length of the at least one UVC lamp;

a fan disposed in the upper portion of the housing and operative to cause air to flow from the surrounding atmosphere downward in the housing and out through the array of vent openings on each side wall and across substantially the full length of each adjacent at least one UVC lamp into the surrounding atmosphere outside of the elongated housing;

the UVC radiation being effective to simultaneously kill pathogens in the air of the surrounding atmosphere outside of the elongated housing and on radiated surfaces in the surrounding atmosphere outside of the elongated housing;

the flowing air being effective to cool the one or more lamps to an optimum operating temperature to maximize the UVC radiation output from the one or more lamps; and a power source coupled to the connectors for energizing the UVC lamps and fan.

\* \* \* \* \*